(12) United States Patent
Kim et al.

(10) Patent No.: US 10,709,752 B2
(45) Date of Patent: Jul. 14, 2020

(54) COMPOSITION COMPRISING THE EXTRACT OF HERBS FOR PREVENTING OR TREATING NEURODEGENERATIVE DISORDERS

(71) Applicant: DONG-A ST CO., LTD., Seoul (KR)

(72) Inventors: Soon-Hoe Kim, Suwon-si (KR);
Mi-Won Son, Yongin-si (KR);
Sang-Zin Choi, Yongin-si (KR);
Hye-Ju Kim, Hwaseong-si (KR);
Ja-Young Ryu, Seoul (KR); Sun-Yeou Kim, Seoul (KR)

(73) Assignee: DONG-A ST CO., LTD. (KR)

( * ) Notice: Subject to any disclaimer, the term of this patent is extended or adjusted under 35 U.S.C. 154(b) by 449 days.

(21) Appl. No.: 15/484,034

(22) Filed: Apr. 10, 2017

(65) Prior Publication Data

US 2017/0216390 A1 Aug. 3, 2017

Related U.S. Application Data

(62) Division of application No. 14/003,077, filed as application No. PCT/KR2011/010290 on Dec. 29, 2011, now abandoned.

(30) Foreign Application Priority Data

Mar. 16, 2011 (KR) .......................... 10-2011-0023545

(51) Int. Cl.
| | |
|---|---|
| *A61K 36/8945* | (2006.01) |
| *A23L 33/105* | (2016.01) |
| *A23L 2/52* | (2006.01) |
| *A61K 9/00* | (2006.01) |
| *A61K 9/08* | (2006.01) |
| *A61K 9/20* | (2006.01) |
| *A61K 9/48* | (2006.01) |

(52) U.S. Cl.
CPC ............ *A61K 36/8945* (2013.01); *A23L 2/52* (2013.01); *A23L 33/105* (2016.08); *A61K 9/0019* (2013.01); *A61K 9/08* (2013.01); *A61K 9/20* (2013.01); *A61K 9/48* (2013.01); *A23V 2002/00* (2013.01); *A61K 2236/15* (2013.01); *A61K 2236/333* (2013.01); *A61K 2236/51* (2013.01); *A61K 2236/53* (2013.01)

(58) Field of Classification Search
CPC .................................................. A61K 36/8945
See application file for complete search history.

(56) References Cited

U.S. PATENT DOCUMENTS

| | | | |
|---|---|---|---|
| 8,202,554 B2 | 6/2012 | Kim et al. ..................... 424/725 |
| 2009/0041865 A1 | 2/2009 | Kim et al. ..................... 424/725 |
| 2013/0072459 A1 | 3/2013 | An et al. .......................... 514/81 |
| 2013/0085160 A1 | 4/2013 | Kim et al. ..................... 546/229 |
| 2013/0296571 A1 | 11/2013 | Son et al. ....................... 546/75 |
| 2013/0317052 A1 | 11/2013 | Son et al. ..................... 514/289 |
| 2014/0017345 A1 | 1/2014 | Kim et al. ..................... 424/725 |
| 2014/0044817 A1 | 2/2014 | Kim et al. | |
| 2014/0155609 A9 | 6/2014 | Son et al. ....................... 546/75 |
| 2017/0209515 A1 | 7/2017 | Kim et al. | |
| 2018/0318377 A1 | 11/2018 | Kim et al. | |

FOREIGN PATENT DOCUMENTS

| | | |
|---|---|---|
| KR | 10-2007-0018570 | 2/2007 |
| KR | 10-0811683 | 3/2008 |
| KR | 10-0854621 | 8/2008 |
| KR | 10-2010-0002668 | 1/2010 |
| KR | 10-2010-0084926 | 7/2010 |
| WO | WO 2007/049932 | 5/2007 |
| WO | WO 2012/124888 | 9/2012 |

OTHER PUBLICATIONS

Rowe et al. "Propylparaben" and "Sodium Metabisulfate" from "Handbook of Pharmaceutical Excipients". pp. 596-598 and 654-655. (Year: 2009).*
Huck et al. Am. J. Hum. Genet. 74:745-751. (Year: 2004).*
Letter/Written Disclosure of the Information Disclosure Statement for the above-referenced application, filed herewith on Jun. 9, 2017, 2 pages.
Bemelmans et al., "Brain-derived neurotrophic factor-mediated protection of striatal neurons in an excitotoxic rat model of Huntington's disease, as demonstrated by adenoviral gene transfer," Hum. Gene Ther. 10(18):2987-2997 (1999).
Choi et al., "Novel botanical drug for the treatment of diabetic neuropathy," Arch. Pharm. Res. 34(6):865-867 (2011).
Dawbarn et al., "Neurotrophins and neurodegeneration," Neuropathology and Applied Neurobiology, 29(3):211-230 (2003).
Dong-A Group website, "Pipeline," Copyright 2009 [online][retrieved on Jul. 7, 2013] Retrieved from:<URL:en.donga.co.kr/rnd/rnd03.jsp, 2 pages.
Dong-A Group website, "R&D at Dong-A," Copyright 2009 [online][retrieved on Jul. 7, 2013] Retrieved from:<URL:en.donga.co.kr/rnd/rnd01.jsp , 1 page.
Dong-A Group website, "Research Center," Copyright 2009 [online][retrieved on Jul. 7, 2013] Retrieved from:<URL:en.donga.co.kr/rnd/rnd02.jsp, 2 pages.
Emard et al., "Neurodegenerative diseases and risk factors: a literature review," Soc. Sci. Med. 40(6):847-858 (1995).

(Continued)

*Primary Examiner* — Amy L Clark
(74) *Attorney, Agent, or Firm* — Sterne, Kessler, Goldstein & Fox P.L.L.C.

(57) ABSTRACT

This invention relates to a pharmaceutical composition and a health functional food for preventing or improving neurodegenerative disorders comprising mixed herb extracts of *Dioscorea Rhizoma* and *Dioscorea nipponica* in a weight ratio of 3.5:1 (w/w). The herb extracts mixed *Dioscorea Rhizoma* and *Dioscorea nipponica* in a weight ratio of 3.5:1 have the synergetic effects on increasing the amount of nerve growth factor in vivo, increasing the neural cell proliferation, promoting the formation of neuritis and enhancing cognitive abilities. Thus, the herb extracts of the present invention may be used for a pharmaceutical composition and a health functional food for preventing or treating neurodegenerative disorders.

14 Claims, 1 Drawing Sheet

(56) References Cited

OTHER PUBLICATIONS

English language abstract of Korean Patent No. KR 10-0811683 (Korean Patent Application No. 10-2006-0115301), Korean Intellectual Property Office, 2 pages.
Fischer et al., "Amelioration of cholinergic neuron atrophy and spatial memory impairment in aged rats by nerve growth factor," Nature 329(6134):65-68 (1987).
Ji et al., "Evaluation of DA-9801, a new herbal drug for diabetic neuropathy, on metabolism-mediated interaction," Arch. Pharm. Res. 36(1):1-5 (2013).
Joshi et al., "Classification of neurodegenerative disorders based on major risk factors employing machine learning techniques," International Journal of Engineering and Technology 2(4):350-355 (2010).
Kang et al., "Characteristics of antidiabetic effects of Dioscorea rhizoma(2)—Prevention of diabetic neuropathy by NGF induction—" Korean J. Food & Nutr. 21(4):430-435 (2008) [article in Korean; includes an English Language abstract].
Kang et al., "Diosgenin from dioscorea nipponica ameliorates diabetic neuropathy by inducing nerve growth factor," Biological and Pharmaceutical Bulletin 34(9):1493-1498 (2011).
Kim et al., "Furostanol saponins from the rhizomes of Dioscorea japonica and their effects on NGF induction," Bioorganic & Medicinal Chemistry Letters 21(7):2075-2078 (2011).
Kim et al., "Neurotrophic activity of DA-9801, a mixture extract of Dioscorea japonica Thunb. and Dioscorea nipponica Makino, in vitro," Journal of Ethnopharmacology 137(1):312-319 (2011).
Lindsay, R., "Neurotrophic growth factors and neurodegenerative diseases: therapeutic potential of the neurotrophins and ciliary neurotrophic factor," Neurobiol. Aging 15(2):249-251 (1994).
Mitsumoto et al., "Arrest of motor neuron disease in wobbler mice cotreated with CNTF and BDNF," Science 265(5175):1107-1110 (1994).
Seeburger, J. and J. Springer, "Experimental rationale for the therapeutic use of neurotrophins in amyotrophic lateral sclerosis," Exp. Neurol. 124(1):64-72 (1993).
Sendtner et al.,"Brain-derived neurotrophic factor prevents the death of motor neurons in newborn rats after nerve section," Nature 360(6406):757-759 (1992).
Song et al., "Evaluation of the transporter-mediated herb-drug interaction potential of DA-9801, a standardized dioscorea extract for diabetic neuropathy, in human in vitro and rat in vivo," BMC Complement. Altern. Med. 14:251, 9 pages (2014).
Yang et al., "Phytochemical and pharmacological profiles of *Dioscorea* species in Korea, China and Japan," Korean Journal of Pharmacognosy 40(4):257-279 (2009) [article in Korean; includes an English Language abstract].
Zuccato et al., "Loss of Huntington-mediated BDNF gene transcription in Huntington's disease," Science 293(5529):493-498 (2001).
International Search Report and Written Opinion, dated Aug. 31, 2012, in connection with International Patent Application No. PCT/KR2011/010290, 6 pages.
International Search Report and Written Opinion, dated Aug. 31, 2012, in connection with International Patent Application No. PCT/KR2011/010294, 6 pages.
International Preliminary Report on Patentability, dated Sep. 17, 2013, in connection with International Patent Application No. PCT/KR2011/010290, 4 pages.
International Preliminary Report on Patentability, dated Sep. 17, 2013, in connection with International Patent Application No. PCT/KR2011/010294, 4 pages.
Extended European Search Report, dated Jul. 28, 2014, in connection with European Patent Application No. 11860864.5, 7 pages.
Extended European Search Report, dated Jul. 23, 2014, in connection with European Patent Application No. 11861135.9, 7 pages.
Office Action, dated Dec. 31, 2015, in connection with U.S. Appl. No. 14/003,077, 10 pages.
Decision to Grant a European Patent Pusuant to Article 97(1) EPC, dated Mar. 24, 2016, in connection with European Patent Application No. 11861135.9, 2 pages.
Response, filed Apr. 29, 2016, to Office Action, dated Dec. 31, 2015, in connection with U.S. Appl. No. 14/003,077, 27 pages.
Office Action, dated Jan. 12, 2016, in connection with U.S. Appl. No. 14/003,087, 10 pages.
Decision to Grant a European patent pusuant to Article 97(1) EPC, dated Mar. 24, 2016, in connection with European Patent Application No. 11860864.5, 2 pages.
Response, filed May 2, 2016, to Office Action, dated Jan. 12, 2016, in connection with U.S. Appl. No. 14/003,087, 22 pages.
Final Office Action, dated Aug. 3, 2016, in connection with U.S. Appl. No. 14/003,087, 16 pages.
Final Office Action, dated Aug. 4, 2016, in connection with U.S. Appl. No. 14/003,077, 16 pages.
Request for Continued Examination and Preliminary Amendment, filed Nov. 3, 2016, in response to Final Office Action, dated Aug. 4, 2016, in connection with U.S. Appl. No. 14/003,077, 20 pages.
Request for Continued Examination and Preliminary Amendment, submitted Nov. 3, 2016, in response to Final Office action, dated Aug. 3, 2016, in connection with U.S. Appl. No. 14/003,087, 21 pages.
Office Action, dated Jan. 13, 2017, in connection with U.S. Appl. No. 14/003,087, 16 pages.
Office Action, dated Jan. 11, 2017, in connection with U.S. Appl. No. 14/003,077, 16 pages.
Apfel, S., "Neurotrophic factors in the therapy of diabetic neuropathy," Am. J. Med. 107(2B):34S-42S (1999).
Arrieta et al., "Retinoic acid increases tissue and plasma contents of nerve growth factor and prevents neuropathy in diabetic mice," European Journal of Clinical Investigation 35(3):201-207 (2005).
Cole, B., "Diabetic peripheral neuropathic pain: recognition and management," Pain Medicine 8(S2):S27-S32 (2007).
Eglen et al., "Central5-HT 4 receptors," Trends in Pharmacol. Sci. 16:391-398 (1995).
Huck et al., "Ribose-5-Phosphate Isomerase Deficiency: New Inborn Error in the Pentose Phosphate Pathway Associated with a Slowly Progressive leukoencephalopathy," Am. J. Hum. Genet. 74:745-751, The American Society of Human Genetics (2004).
Rubino et al., "Diagnosis of diabetic peripheral neuropathy among patients with type 1 and type 2 diabetes in France, Italy, Spain, and the United Kingdom," Primary Care Diabetes 1 (3): 129-134 (2007).
Rowe et al. "Propylparaben" and "Sodium Metabisulfate," Handbook of Pharmaceutical Excipients, Sixth edition, pp. 596-598 and 654-655, Pharmaceutical Press (2009).
The Diabetes Control and Complications Trial Research Group, "The effect of intensive treatment of diabetes on the development and progression of long-term complications in insulin-dependent diabetes mellitus," N. Engl. J. Med. 329:977-986 (1993).
Varkonyi, T. And Kempler, P., "Diabetic neuropathy: new strategies for treatment," Diabetes Obes. Metab. 10(2):99-108 (2008).
Wong et al., "Effects of treatments for symptoms of painful diabetic neuropathy: systematic review," BMJ 335(7610):87, 10 pages (2007).

\* cited by examiner

Control group     10     100

The mixed herb extracts of D.Rhizoma : D.Nipponica 3.5 : 1

COMPOSITION COMPRISING THE EXTRACT OF HERBS FOR PREVENTING OR TREATING NEURODEGENERATIVE DISORDERS

RELATED APPLICATIONS

This application is a divisional of co-pending U.S. patent application Ser. No. 14/003,077, lodged on Sep. 4, 2013 and having a 371(c) date of Oct. 3, 2013, which is the U.S. national stage of International Application No. PCT/KR2011/010290, having an international filing date of Dec. 29, 2011, which claims priority to Korean Patent Application No. 10-2011-0023545, filed Mar. 16, 2011, the subject matter of each of which is incorporated by reference in its entirety.

TECHNICAL FIELD

This invention relates to a composition comprising the extract of herbs for preventing or treating neurodegenerative disorders, wherein it comprises *Dioscorea Rhizoma* and *Dioscorea nipponica* mixed in a weight ratio of 3.5:1 (w/w).

ACKNOWLEDGEMENT

This work was supported by the Global Leading Technology Program of the Office of Strategic R&D Planning (OSP) funded by the Ministry of Knowledge Economy, Republic of Korea. (No. 10039303)

BACKGROUND ART

Neurodegenerative disorders mean a gradually structural and functional loss of a nerve cell (neuron). They usually affect a particular part of the nervous system, accompanying the symptoms such as dementia, extrapyramidal disease, cerebellar disorder, dysesthesia or dyskinesia. The complex symptoms may be shown when affecting the various parts at the same time. A diagnosis is gotten by a patient's clinical sign. However, the diagnosis in this case is difficult to make because it shows multiple symptoms and the varied diseases have the common clinical signs. (Soc. Sci. Med. Vol. 40. No. 6, pp. 847-585, 1995).

Signs of the onset of neurodegenerative disorders appear gradually and mostly occur with aging. Once an outbreak, neurodegenerative disorders progress for several years or decades until death. It is known that the genetic effects according to a family history are considerable. According to the clinical symptoms, degenerative disorders are classified into paralytic dementia (Alzheimer's disease etc.), neurologic disorder (Pick's disease etc.), abnormalities in posture and exercise (Parkinson's disease etc.), progressive ataxia, muscular atrophy and weakness, and sensation and movement disorders. (International Journal of Engineering and Technology, Vol. 2, No. 4, Aug. 2010 Classification of Neurodegenerative Disorders Based on Major Risk Factors Employing Machine Learning Techniques).

In 1980s, it was raised that neurotrophic factors have the potential to treat neurodegenerative disorders as Alzheimer's disease experiment (Nature. 1987 Sep. 3-9; 329(6134): 65-8. Amelioration of cholinergic neuron atrophy and spatial memory impairment in aged rats by nerve growth factor) The loss of neuron of basal forebrain by aging known as Alzheimer's disease is recovered by administration of nerve growth factor (NGF) to the lateral ventricle of the brain. As the memory improvement of tested animals is reported, the studies for treating neurodegenerative disorders are conducted by using neurotrophic factor. It met with a good result that the function of motor neurons damaged by Brain-derived neurotrophic factor (BDNF), Neurotrophin-3 (NT-3), Neurotrophin-4 (NT-4), and Ciliary neurotrophic factor (CNTF) as neurotrophic factor family is recovered in the study after hurting the function of the motor neurons by sectioning the facial nerves and the sciatic nerves as the follow-up study. (Nature. 1992 Dec. 24-31; 360(6406):757-9. Brain-derived neurotrophic factor prevents the death of motor neurons in newborn rats after nerve section.). In the experiment used gene recombination mice (wobbler) which suffered from losing its motor neurons and function gradually, the function was enhanced by administrating BDNF and CNTF to increase the number of motor neurons. (Science. 1994 Aug. 19; 265(5175):1107-10. Arrest of motor neuron disease in wobbler mice cotreated with CNTF and BDNF). Besides the said experiments, neurotrophic factors increase neurons and their function in the pathological model of motor neurons and various senses, so it showed the improvement of disorder related to memory, perception, and behavior in the laboratory animals.

Based on the results of pre-clinical experiments, there were trials to apply neurotrophic factor for the treatment of Lou Gehrig's disease in 1990s. Lou Gehrig's disease is a degenerative nervous disease which only motor neurons die out selectively and makes human die due to the dysfunction of respiratory organs with paralysis of the whole body. BDNF was hypodermically or subarachnoidally administered, however, a pain of injection region and the side effect of digestive system was shown. So, there had been no choice but to administer the smaller amount of BDNF than the pre-clinical experiment. As a result, the regeneration and improvement of motor neuron and its function had minimal effect. (Exp Neurol. 1993 Nov.;124(1):64-72. Review. Experimental rationale for the therapeutic use of neurotrophins in amyotrophic lateral sclerosis). Similarly, symptoms such as a fever, a pain of injection region or a loss of appetite which were more severe adverse reactions than the case of administration of BDNF were shown when CNTF was injected to the patient suffered from Lou Gehrig's disease, therefore CNTF was administered with a limited amount. As a result, the regeneration and improvement of motor neuron and its function was insignificant. (Neurobiol Aging. 1994 Mar.-Apr.; 15(2):249-51. Review Neurotrophic growth factors and neurodegenerative diseases: therapeutic potential of the neurotrophins and ciliary neurotrophic factor). The method of having neurotrophic factor such as BDNF, CNTF, etc as a form of the recombinant protein reach the central and peripheral nervous system by injecting in vivo had the limited amount of injecting protein. In case of the experiment which attempted to treat the patient having Alzheimer's disease using NGF, it couldn't show the significant result since there were side effects, the limit of injecting amount, the drug delivery and uncertain pharmacodynamics.

Although a disappointing result of the clinical experiment, there have been many experimental evidences which are possible to treat neurodegenerative disorders using neurotrophic factors. Typically, in case of Huntington's disease, which its symptoms are abnormal movements, personality changes, decreased cognitive ability, and early death due to increasing poly Q in Huntington protein, a lot of studies noted BDNF as a main target of abnormal Huntington protein. This theory was supported by decreasing the amount of BDNF in the striatum of the pathological laboratory animals and the patient having Huntington's disease. (Science. 2001 Jul. 20;293(5529):493-8. Epub 2001 Jun. 4 Loss of Huntington-mediated BDNF gene transcription in Huntington's disease).

By the way, when the method to administer neurotrophic factor hypodermically or subarchnoidally in vivo with the form of a recombinant protein as same as the existing method in order to treat degenerative disorders was chosen, decreasing the amount of administration and reducing its effect were repeated due to the side effect. Therefore the studies of neurotrophic factor enhancer which is indirect way to increase the amount of neurotrophic factor biosynthesized itself in vivo in 2000s. (Hum Gene Ther. 1999 Dec. 10;10(18):2987-97. Brain-derived neurotrophic factor-mediated protection of striatal neurons in an excitotoxic rat model of Huntington's disease, as demonstrated by adenoviral gene transfer).

Dioscorea Rhizoma, a plant belonging to Dioscoreaceae, is the telin for fresh rhizome of Dioscorea batatas Decaisne or Dioscorea japonica Thunberg, void of periderm, or for that obtained after the fresh rhizome was steamed and dried in the herbal medicine. It is widely distributed in Korea, China, and Japan, and was used as a medicine. It has remedial effects on tonic nutrition, digestive disorders, diabetes, cough, pulmonary disease, strengthening kidney function, etc and toxicity and side effects often have not released. Moreover, *Dioscorea nipponica* is a rhizome of *Dioscorea nipponica* Makino, a climbing perennial plant of Dioscoreaceae. It is widely distributed in Korea, China, and Japan, and was used as a medicine. It has effects on better circulation of blood, loosening the muscles, removing indigestion, keeping one's urine open, removing sputum, and prevention of malaria paroxysm and toxicity and side effects often have not released.

Korean Patent No. 854621 provides a composition for the prevention and treatment of peripheral neuropathy, comprising an extract from a plant selected from among *Dioscorea nipponica, Dioscorea quinqueloba, Dioscorea batatas, Dioscorea japonica* and *Dioscorea tokora*, disclosing that the composition induces the growth of neurites and increases the secretion of endogenous nerve growth factor, thus being effective for preventing or treating peripheral neuropathy.

The present inventors confirmed that the function of the extract from a plant selected from among *Dioscorea nipponica, Dioscorea quinqueloba, Dioscorea batatas, Dioscorea japonica* and *Dioscorea tokora* was to induce the significant growth of neurites and to increase the secretion of endogenous NGF as disclosed in Korean Patent No. 854621. Based on that, the present invention has been completed after ascertaining that *Dioscorea Rhizoma* and *Dioscorea nipponica* in the selectively particular ratio show very significant synergism although the said herbs each or their mixed herb extracts surprisingly induce almost same growth of neurites as well as increase the secretion of endogenous nerve growth factor while studying a herb extract which has effects on neural cell proliferation, promotion of neuritis formation and enhancing cognitive abilities by increasing the contents of nerve growth factor in the laboratory animals in vivo.

DISCLOSURE OF INVENTION

Technical Problem

It is therefore an object of the present invention to provide an optional herbal composition which shows the synergy to enhance cognitive abilities by increasing the neural cell proliferation and promoting the formation of neuritis after stimulating the production and secretion of nerve growth factors, among the herbs disclosed in Korean Patent No. 854621, to enhance the regeneration and prevent apoptosis of neurons.

It is another object of the present invention to provide a pharmaceutical composition and a health functional food for preventing or treating neurodegenerative disorders, comprising the said herb composition as an active ingredient.

Solution to Problem

In accordance with an aspect of the present invention, there is provided a pharmaceutical composition and a health functional food for preventing or treating neurodegenerative disorders comprising a mixed extract of *Dioscorea Rhizoma* and *Dioscorea nipponica* in a weight ratio of 3.5:1 (w/w).

Hereinafter, the present invention will be described in detail.

The present invention relates to a pharmaceutical for preventing or treating neurodegenerative disorders comprising a mixed extract of *Dioscorea Rhizoma* and *Dioscorea nipponica* in a weight ratio of 3.5:1 (w/w).

The mixed extract of *Dioscorea Rhizoma* and *Dioscorea nipponica* in a weight ratio of 3.5:1 (w/w) compared to the total weight is a crude extract, which is an extract preferably extracted with 50% of ethanol.

The extracts of *Dioscorea Rhizoma* and *Dioscorea nipponica* may be obtained as below. First, herbs were prepared by cutting dried herbs after cleaning and drying Dioscorea Rhizoma and *Dioscorea nipponica* respectively. Then, the mixed herb extracts of *Dioscorea Rhizoma* and *Dioscorea nipponica* in a weight ratio of 3.5:1 (w/w) could be obtained by concentration under reduced pressure after one time of cold extraction for 48 hours in a room temperature with 50% of ethanol 5 times more than the total weight of the said cutting herbs.

The present invention provides the use of herb extracts mixed with *Dioscorea Rhizoma* and *Dioscorea nipponica* in a weight ratio of 3.5:1 (w/w) for preparing a pharmaceutical composition for preventing or treating neurodegenerative disorders.

The examples of neurodegenerative disorders by the present invention include Alzheimer's disease, Creutzfeldt-Jakob disease, Huntington's disease, multiple sclerosis, Guillain-Barre syndrome, Parkinson's disease, Lou Gehrig's disease, paralytic dementia caused by gradual nerve cell death and diseases caused by progressive incontinentia.

According to the present invention, a pharmaceutical preparation for preventing or treating neurodegenerative disorders can be formulated by adding a pharmaceutically acceptable carrier, diluent or diluting agent to the mixed herb extracts of *Dioscorea Rhizoma* and *Dioscorea nipponica* in a weight ratio of 3.5:1 (w/w).

The herb extracts needed to formulate a pharmaceutical preparation of the present invention include 0.01 to 80% of the said extracts, preferably 1 to 50% by weight compared to the total weight.

The carrier, diluent or diluting agent which can be included in the composition of the present invention may be lactose, dextrose, sucrose, sorbitol, mannitol, xylitol, erythritol, maltitol, starch, gum Acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil.

Furthermore, the composition of the present invention can be formulated and used in forms of oral agent such as powder, granules, tablets, capsules, suspension, emulsion, syrup or aerosol, external preparation, suppository or sterile injecting solution according to the ordinary method.

Specifically, a pharmaceutical preparation could be prepared by using diluents or diluting agents such as filter, extender, binding agent, moistening agent, disintegrating agent or surfactant which are commonly used. The solid pharmaceutical preparation for oral administration includes tablets, pills, powder, granules and capsules. The solid pharmaceutical preparation can be formulated by adding at least one or more diluting agents such as starch, calcium carbonate, sucrose, lactose or gelatin to the said herb complex. Moreover, lubricants such as magnesium stearate or talc aside from the said diluting agents. The liquid pharmaceutical preparation includes suspension, liquid medicine for internal use, emulsion or syrup. It could include the various diluting agents such as moistening agent, sweetening agent, air freshener or preserved agent aside from the simple diluents such as water and liquid paraffin which are commonly used. A pharmaceutical preparation for parenteral administration includes sterile solution, nonaqueous solvent, suspension, emulsion, lyophilized agent or suppository. Propyl glycol, polyethylene glycol, vegetable oil like olive oil or injectable ester like ethylolate could be used for nonaqueous solvent or suspension. For suppository, witepsol, polyethylene glycol, tween 61, cacao butter, laurinum or glycerol-gelatin could be used.

In accordance with another aspect of the present invention, there is provided a method for treatment of neurodegenerative disorders, wherein a pharmaceutical composition comprising the herb extracts mixed with *Dioscorea Rhizoma* and *Dioscorea nipponica* in a weight ratio of 3.5:1 as an active ingredient is administered to mammals including human with a pharmaceutically active amount.

The dosage of the pharmaceutical composition comprising the herb extracts mixed with *Dioscorea Rhizoma* and *Dioscorea nipponica* in a weight ratio of 3.5:1 depends on age, sex and weight of a patient, however, can be administered with an amount of 0.01 to 10 g/kg, preferably 1 to 5 g/kg which amount is administered once a day or divided into many times a day. Also, the dosage can be increased or decreased according to injection route, degree of disease, sex, weight, age, health condition, diet, injection time, injection method or excretion rate. Therefore the dosage is in no way intended to limit the scope of the present invention.

The pharmaceutical composition comprising the herb extracts mixed with *Dioscorea Rhizoma* and *Dioscorea nipponica* in a weight ratio of 3.5:1 (w/w) of the present invention may be administered to mammals such as rats, mice, cattle or human through the various routes. All the way of administration may be expected, for example, oral, rectal or vein, intramuscular, hypodermic, endometrial or intracerebroventicular injections.

The herb extracts mixed with *Dioscorea Rhizoma* and *Dioscorea nipponica* in a weight ratio of 3.5:1 of the present invention has almost never show toxicity or side effects, thus, it is safe to take a dose for a long time for the purpose of prevention.

The inventors have studied the effects on neural cell proliferation, promoting the formation of neurites and enhancing cognitive abilities by increasing the amount of nerve growth factors in the laboratory animals, using the herb extracts mixed with *Dioscorea Rhizoma* and *Dioscorea nipponica* in a weight ratio of 3.5:1. Then, they have found the significant synergism compared with a single extract of *Dioscorea Rhizoma* and *Dioscorea nipponica* and other ratio of them by experiencing the laboratory animal model or cells.

Furthermore, the present invention provides a health functional food for preventing or improving neurodegenerative disorders.

As used herein, the term "health functional food" is intended to include those defined in the "2002 Law for health functional foods," such as health foods found in the list stipulating health functional food materials or ingredients verified for functionally and safety for humans according to KFDA Notice No. 2004-12 of the Korean Food and Drug Administration.

More particularly, the present invention provides a health functional food for preventing or improving neurodegenerative disorders, comprising the herb extracts mixed with *Dioscorea Rhizoma* and *Dioscorea nipponica* in a weight ratio of 3.5:1 and a sitologically acceptable food additive.

The composition comprising the herb extracts mixed with *Dioscorea Rhizoma* and *Dioscorea nipponica* in a weight ratio of 3.5:1 can be applied to drugs, foods and drink for alleviating symptoms of neurodegenerative disorders. For example, the foods to which the herb extract of the present invention can be added include beverages, gum, teas, vitamin complexes, and food aids. For use in drugs, the herb extract may be in the form of pills, powders, granules, tablets, capsules or liquids.

When applied to solid foods, the herb extract of the present invention may be used in an amount of food from 0.1 to 15% by weight based on the total weight of the food, and preferably in an amount of from 0.2 to 10% by weight. In a liquid form of health, the herb extract of the present invention may range in amount from 0.1 to 30 g per 100 mL of the liquid and preferably from 0.2 to 5 g.

Except for the specific ratio given to the indispensable herb ingredients, no particular limitations are imparted to the liquid health composition. Like typical beverages, the liquid health composition may further comprise various flavoring agents, natural carbohydrates, or other additives.

Preferable examples of the natural carbohydrates include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. The flavoring agents useful in the present invention may be natural (thaumatin, stevia extract (e.g., rebaudioside A, glycyrrhizin), or synthetic (saccharin, aspartame). Natural carbohydrates may be used in an amount of from about 1 to 20 g per 100 mL of the liquid health composition, and preferably in an amount of from about 5 to 12 g.

In addition, the composition of the present invention may contain various nutrients, vitamins, minerals (electrolytes), synthetic and/or natural flavoring agents, colorants, fillers (cheese, chocolate, etc.), pectic acid and its salts, alginic acid and its salts, organic acids, protective colloidal thickeners, pH modifiers, stabilizers, preservatives, glycerin, alcohols, and carbonating agents for carbonate beverages. For use in natural fruit juice, fruit juice beverages or vegetable beverages, the composition of the present invention may further contain fruit flesh. These additives may be used alone or in combination. Typical, but unimportant, amounts of the additives are on the order of from 0 to 20 parts by weight per 100 parts by weight of the composition.

Advantageous Effects of Invention

The herb extracts mixed *Dioscorea Rhizoma* and *Dioscorea nipponica* in a weight ratio of 3.5:1 have the synergetic effects on increasing the amount of nerve growth factor (NGF) in vivo, increasing the neural cell proliferation, promoting the formation of neurites and enhancing cognitive abilities. Thus, the herb extracts of the present invention may be used for a pharmaceutical composition and health food for preventing or improving neurodegenerative disorders.

MODE FOR THE INVENTION

The present invention will now be described in further detail by examples. It would be obvious to those skilled in the art that these examples are intended to be more concretely illustrative and the scope of the present invention as set forth in the appended claims is not limited to or by the example.

EXAMPLE 1

Preparation of the Mixed Herb Extracts of *Dioscorea Rhizoma* and *Dioscorea nipponica*.

*Dioscorea Rhizoma* and *Dioscorea nipponica*, both in a dry condition, were purchased from a herb medicine shop in Kyoungdong market, Korea. After impurities were removed therefrom, the herbs were chopped with a cutter and mixed at a weight ratio of 3.5:1 *Dioscorea Rhizoma: Dioscorea nipponica*. To 2 kg of the mixture was added 10 L of a 50% ethanol solution, followed by incubation at room temperature for 48 hours with stirring. The herb mixture was removed by filtration, and the filtrate was concentrated in a vacuum and freeze dried to afford a mixed herb extract (crude extract) (see Table 1).

TABLE 1

Yield of the mixed herb extracts

| | Amount *D. Rhizoma* | Amount *D. nipponica* | Solvent | Amount of solvent | wash | Extraction temperature | Extraction time | Result (g) | Yield (%) |
|---|---|---|---|---|---|---|---|---|---|
| Example 1 | 1.55 kg | 0.45 kg | 50% EtOH | 10 L | 1 L | Room Temperature | 2 days | 212.85 | 10.64 |

COMPARATIVE EXAMPLES 1 and 2

Preparation of Crude Herb Extracts
1. Preparation of Crude Extract of *Dioscorea Rhizoma*
2 kg of the same *Dioscorea Rhizoma* used in EXAMPLE 1 and stirred 2 kg of the same *Dioscorea Rhizoma* used in Example 1 and stirred 10 L of 50% ethanol solution was added to for 48 hours at room temperature. The extract of *Dioscorea Rhizoma* crude extract was finally obtained by lyophilization after extracting, filtering and concentrating under reduced pressure (See Table 2).

TABLE 2

Yield of the extract of *Dioscorea Rhizoma*

| | Amount of herb | Solvent | Amount of solvent | Clean | Extraction Temperature | Extraction Time | Result (g) | Yield (%) |
|---|---|---|---|---|---|---|---|---|
| Comparative Example 1 | 2 kg | 50% EtOH | 10 L | 1 L | Room temperature | 2 days | 253.8 | 12.69 |

2. Preparation of Crude Extract of *Dioscorea nipponica*

10 L of 50% ethanol solution was added to 2 kg of the same *Dioscorea nipponica* used in Example 1 and stirred for 48 hour at room temperature. The extract of *Dioscorea nipponica* (crude extract) was finally obtained by lyophilization after extracting, filtering and concentrating under reduced pressure (See Table 3).

TABLE 3

Yield of the extract of *Dioscorea nipponica*

| | Amount of herb | Solvent | Amount of solvent | Wash | Extraction Temperature | Extraction Time | Result (g) | Yield (%) |
|---|---|---|---|---|---|---|---|---|
| Comparative Example 2 | 2 kg | 50% EtOH | 10 L | 1 L | Room temperature | 2 days | 160 | 8.00 |

COMPARATIVE EXAMPLES 3 to 10

Preparation of the Mixed Herb Extract of *Dioscorea Rhizoma* and *Dioscorea nipponica*

The same herbs *Dioscorea Rhizoma* and *Dioscorea nipponica* as used in Example 1 were used. *Dioscorea Rhizoma* and *Dioscorea nipponica* were chopped with a cutter and mixed at the weight ratios listed in Table 4. To 2 kg of each of the mixtures was added 10 L of a 50% ethanol solution, followed by incubation at room temperature for 48 hours with stirring. The herb mixtures were removed by filtration, and the filtrate was concentrated in a vacuum and freeze dried to afford mixed herb extracts (crude extracts). (See Table 4).

TABLE 4

Yield of the mixed herb extracts.

| | Amount of herb (kg) | | | | | | | | |
|---|---|---|---|---|---|---|---|---|---|
| | D. Rhizoma | D. nipponica | Solvent | Amount of solvent | Wash | Extraction Temperature | Extraction Time | Result (g) | Yield (%) |
| Comparative Example 3 | 1 | 1 | 50% EtOH | 10 L | 1 L | Room temperature | 2 days | 179.05 | 8.95 |
| Comparative Example 4 | 1.33 | 0.67 | 50% EtOH | 10 L | 1 L | Room temperature | 2 days | 135.96 | 6.80 |
| Comparative Example 5 | 1.67 | 0.33 | 50% EtOH | 10 L | 1 L | Room temperature | 2 days | 160.07 | 8.00 |
| Comparative Example 6 | 1.82 | 0.18 | 50% EtOH | 10 L | 1 L | Room temperature | 2 days | 138.75 | 6.93 |
| Comparative Example 7 | 0.67 | 1.33 | 50% EtOH | 10 L | 1 L | Room temperature | 2 days | 153.56 | 7.68 |
| Comparative Example 8 | 0.45 | 1.55 | 50% EtOH | 10 L | 1 L | Room temperature | 2 days | 139.15 | 6.96 |
| Comparative Example 9 | 0.33 | 1.67 | 50% EtOH | 10 L | 1 L | Room temperature | 2 days | 181.06 | 9.05 |
| Comparative Example 10 | 0.18 | 1.82 | 50% EtOH | 10 L | 1 L | Room temperature | 2 days | 146.43 | 7.32 |

EXPERIMENTAL EXAMPLE 1

Effect of the Herb Extracts on Increasing the Secretion of Nerve Growth Factor

The effects on increasing and enhancing the secretion of NGF by Example 1 was identified by using C6 glioma, a cell strain of neuroglioma of rats producing NGF. Comparative examples 1 to 10 were the control groups of this experiment.

C6 cell was cultured in 24-well cell culture plate with medium, DMEM (adding 5% FBS, 2 mM L-glutamine, 10 mM HEPES, 1 mM sodium pyruvate, 50 μg streptomycin, 100 U/ml penicillin) in 37° C. and 5% of $CO_2$. After adjusting the cultured cell in the $2\times10^5$ cell/well concentrations, Example 1, Comparative examples 1 to 10 were treated by 100, 250, and 500 μg/ml. In the same culture condition, the cell was cultured for 2 days and then the concentration of NGF in the medium was measured by using ELISA. (See Table 5).

TABLE 5

Effects on increasing the secretion of NGF

| | D. Rhizoma:D. nipponica compared to the total weight | Concentration (μg/ml) | Concentration of NGF (% of control) |
|---|---|---|---|
| Example 1 | 3.5:1 | 100 | 122 |
| | | 250 | 149 |
| | | 500 | 156 |
| Comparative Example 1 | D. Rhizoma crude extract | 100 | 112 |
| | | 250 | 126 |
| | | 500 | 135 |
| Comparative Example 2 | D. nipponica crude extract | 100 | 102 |
| | | 250 | 121 |
| | | 500 | 130 |
| Comparative Example 3 | 1:1 | 100 | 108 |
| | | 250 | 124 |
| | | 500 | 141 |
| Comparative Example 4 | 2:1 | 100 | 117 |
| | | 250 | 131 |
| | | 500 | 136 |
| Comparative Example 5 | 5:1 | 100 | 115 |
| | | 250 | 129 |
| | | 500 | 134 |
| Comparative Example 6 | 10:1 | 100 | 112 |
| | | 250 | 129 |
| | | 500 | 134 |
| Comparative Example 7 | 1:2 | 100 | 107 |
| | | 250 | 116 |
| | | 500 | 129 |
| Comparative Example 8 | 1:3.5 | 100 | 106 |
| | | 250 | 118 |
| | | 500 | 130 |
| Comparative Example 9 | 1:5 | 100 | 107 |
| | | 250 | 116 |
| | | 500 | 126 |
| Comparative Example 10 | 1:10 | 100 | 105 |
| | | 250 | 116 |
| | | 500 | 125 |

As shown in Table 5, the concentration of NGF was increased according to the concentration of *Dioscorea Rhizoma* and *Dioscorea nipponica*. Also, it was shown that the concentration of NGF in *Dioscorea Rhizoma* (Comparative example 1) was more increased than in *Dioscorea nipponica* (Comparative example 2) so the former showed more significant effect.

Although the concentration of *Dioscorea Rhizoma* 25% less than comparative example 1 (*D.Rhizoma* 200) was injected to Example 1 (*D.Rhizoma:D.nipponica*=155:45), 8.9 to 15.5% of NGF content was increased in the same concentration.

Furthermore, the concentration of NGF in Example 1 was more increased approximately 4.2 to 16.4% than Comparative example 5 (*D.Rhizoma:D.nipponica*=167:33, 5:1) which *Dioscorea Rhizoma* was injected 7.7% more and it was more increased 8.9 to 16.4% than Comparative example 6 (*D.Rhizoma:D.nipponica*=182:18, 10:1) which *Dioscorea Rhizoma* was injected 17.4% more). The amount of NGF in Example 1 was more increased approximately 4.4 to 12.9% than Comparative example 4 (*D.Rhizoma:D.nipponica*=133:67, 2:1) which *Dioscorea Rhizoma* was injected 14.2% less. It showed the significantly increasing content of NGF than other Comparative examples.

Therefore it is found that a pharmaceutical composition of the present invention disorders comprising a mixed extract of *Dioscorea Rhizoma* and *Dioscorea nipponica* in a weight ratio of 3.5:1 can increase the concentration of NGF efficiently compared to other mixed ratio. Thus, it could be used in treating or preventing neurodegenerative disorders.

Hereinafter, the enhancing effects on cell proliferation, formation of neurite and cognitive abilities according to the contents of NGF in the herb extracts of *Dioscorea Rhizoma* and *Dioscorea nipponica* are comparatively experimented. So, the availability for preventing or treating neurodegenerative disorders will be discussed.

EXPERIMENTAL EXAMPLE 2

Effect of the Herb Extracts on Improving Cognitive Abilities

ICR mice (male, 6 age of the weeks, 25-28 g) provided from Daehan Biolink (Chungbuk, Korea) were using after 7 days of being raised and adapted in a clean cage of college of pharmacy in Kyunghee university. They were allowed to have feeds (Daehan Biolink, Chungbuk, Korea) and water freely. The temperature (22±2° C.), humidity (53±3%) and cycle of light and dark (12 hours) were controlled automatically.

10 mice were assigned to each group. Saline was orally administered to mice in the control group in 5 mL per kg of weight. 10, 100 mg/kg of EXAMPLE 1, Comparative examples 1 to 10 respectively melted in saline solution were orally administered to mice in the treatment group. Oral administration was done once a day and 1 hour after the last oral administration, passive avoidance test were conducted as follows.

Passive avoidance test was conducted in the A modified shuttle with two communicating (7×7 cm sliding door built into the separating wall) compartments of equal size and a stainless steel bar floor was used. The right-hand compartment (shock compartment) was painted black to obtain a dark chamber. The left-hand compartment was illuminated by a bulb (24 V; 5 W) installed on the top Plexiglass cover. First day, a light turns on in a bright room and turns off in a dark room. And the inventors opened guillotine door after letting mice stay in a bright room for 10 seconds then measured the time until mice entered a dark room. When mice moved into a dark room, guillotine door closed and 0.3 mA of electrical stimulation was given to them for 3 seconds. After 24 hours, passive avoidance test was demonstrated with the same method and latency time of staying in a bright room was measured. The results are shown in Table 6.

TABLE 6

Effect on improving cognitive abilities in passive avoidance test

| | D. Rhizoma:D. nipponica compared to the total weight | Amount (mg/kg) | Latency Time (sec) |
|---|---|---|---|
| Control Group | — | | 166.18 ± 13.83 |
| Example 1 | 3.5:1 | 10 | 220.17 ± 25.63 |
| | | 100 | 275.87 ± 25.40 |
| Comparative Example 1 | D. Rhizoma crude extract | 10 | 202.84 ± 19.65 |
| | | 100 | 225.28 ± 20.21 |
| Comparative Example 2 | D. nipponica crude extract | 10 | 199.62 ± 17.01 |
| | | 100 | 218.24 ± 18.47 |
| Comparative Example 3 | 1:1 | 10 | 194.86 ± 9.43 |
| | | 100 | 204.19 ± 10.72 |
| Comparative Example 4 | 2:1 | 10 | 202.69 ± 11.24 |
| | | 100 | 231.42 ± 16.55 |
| Comparative Example 5 | 5:1 | 10 | 211.43 ± 18.21 |
| | | 100 | 235.71 ± 21.60 |
| Comparative Example 6 | 10:1 | 10 | 205.33 ± 15.08 |
| | | 100 | 219.93 ± 16.14 |
| Comparative Example 7 | 1:2 | 10 | 186.72 ± 1061 |
| | | 100 | 204.68 ± 14.32 |
| Comparative Example 8 | 1:3.5 | 10 | 196.93 ± 16.58 |
| | | 100 | 209.61 ± 14.41 |
| Comparative Example 9 | 1:5 | 10 | 205.89 ± 12.60 |
| | | 100 | 215.99 ± 18.96 |
| Comparative Example 10 | 1:10 | 10 | 193.53 ± 16.08 |
| | | 100 | 211.74 ± 20.57 |

As shown in Table 6, the retention latency in the *Dioscorea Rhizoma* administrating group was increased than that of *Dioscorea nipponica* administrating group, Example 1 (*D.Rhizoma:D.nipponica*=155:45) increased retention latency 8.9 to 22.2% than Comparative example 1 (*D.Rhizoma* 200), although Example 1 was administered 25% less *Dioscorea Rhizoma* than Comparative example 1 (*D.Rhizoma* 200).

Also, the retention latency according to Example 1 was increased 4.2 to 19% than Comparative example 5 (*D.Rhizoma:D.nipponica*=167:33, 5:1) which *Dioscorea Rhizoma* was injected 7.7% more and it was more increased 7.3 to 25.6% than Comparative example 6 (*D.Rhizoma:D.nipponica*=182:18, 10:1) which *Dioscorea Rhizoma* was injected 17.4% more). The retention latency according to Example 1 was increased 8.9 to 19% than Comparative example 4 (*D.Rhizoma:D.nipponica*=133:67, 2:1) which *Dioscorea Rhizoma* was injected 14.2% less. It showed the memory was increased significantly than other Comparative examples.

Therefore it is found that a pharmaceutical composition of the present invention disorders comprising a mixed extract of *Dioscorea Rhizoma* and *Dioscorea nipponica* in a weight ratio of 3.5:1 has the effects on improving the cognitive abilities compared to other mixed ratio.

EXPERIMENTAL EXAMPLE 3

Effect the Herb Extracts on Enhancing Generation of Neurons

Hippocampi were separated from mice of each group after completing the test of Experimental example 2. 5-bromo-2-deoxyuridine (BrdU, santa cruz, rat origin 1:500) as a first antibody was reacted for one night after dehydrating separated hippocampus with hydrogen peroxide. And then, biotinylated anti-rat (vector, goat origin) was used as a second antibody, and color was developed by using Diaminobenzidine after ABC reaction (ABC kit, vector). The effect on enhancing neuronal cell generation was identified by counting BrdU-positive cells in the area of dentate gyrus in hippocampus. The results are shown in Table 7.

TABLE 7

Effect on enhancing cell generation

| | D. Rhizoma:D. nipponica compared to the total weight | Amount (mg/kg) | BrdU-positive cells (% of control) |
|---|---|---|---|
| Example 1 | 3.5:1 | 10 | 153.79 ± 15.24 |
| | | 100 | 158.59 ± 9.45 |
| Comparative Example 1 | D. Rhizoma crude extract | 10 | 123.81 ± 10.14 |
| | | 100 | 129.42 ± 11.36 |
| Comparative Example 2 | D. nipporica crude extract | 10 | 118.60 ± 8.37 |
| | | 100 | 121.59 ± 8.13 |
| Comparative Example 3 | 1:1 | 10 | 124.25 ± 10.93 |
| | | 100 | 125.86 ± 9.06 |
| Comparative Example 4 | 2:1 | 10 | 128.44 ± 11.65 |
| | | 100 | 136.70 ± 13.28 |
| Comparative Example 5 | 5:1 | 10 | 129.54 ± 12.91 |
| | | 100 | 134.08 ± 14.61 |
| Comparative Example 6 | 10:1 | 10 | 121.08 ± 9.54 |
| | | 100 | 128.57 ± 11.77 |
| Comparative Example 7 | 1:2 | 10 | 120.68 ± 9.27 |
| | | 100 | 124.16 ± 11.36 |
| Comparative Example 8 | 1:3.5 | 10 | 126.39 ± 11.17 |
| | | 100 | 130.28 ± 13.49 |
| Comparative Example 9 | 1:5 | 10 | 124.70 ± 10.25 |
| | | 100 | 128.06 ± 11.59 |
| Comparative Example 10 | 1:10 | 10 | 121.84 ± 13.18 |
| | | 100 | 124.12 ± 12.85 |

As shown in Table 7, *Dioscorea Rhizoma* (Example 1) showed increased the number of BrdU-positive cells than *Dioscorea nipponica* (Comparative example 2) when counting BrdU-positive cells in the area of dentate gyrus in hippocampus. Although the amount of *Dioscorea Rhizoma* was injected to Example 1 25% less than Comparative example 1, the number of BrdU-positive cells were increased approximately 25% more.

Furthermore, the number of BrdU-positive cells were increased approximately 25% more in Example 1 than Comparative example 5 which *Dioscorea Rhizoma* was injected 7.7% more than Example 1 and Comparative example 6 which *Dioscorea Rhizoma* was injected 17.4% more than Example 1. The number of BrdU-positive cells were increased approximately 20% more in Example 1 than Comparative example 4 which *Dioscorea Rhizoma* was injected 14.2% less than Example 1. It showed the significantly increasing the number of BrdU-positive cells than other Comparative examples.

Therefore it is found that a pharmaceutical composition of the present invention disorders comprising a mixed extract of *Dioscorea Rhizoma* and *Dioscorea nipponica* in a weight ratio of 3.5:1 has the effects on enhancing the neuronal cell generation in the area of dentate gyrus compared to other mixed ratio.

EXPERIMENTAL EXAMPLE 4

Effect of the Herb Extracts on Neuronal Cell Differentiation and Enhancing Neurite Growth Hippocampi were separated from mice of each group after completing the test of Experimental example 2. Doublecortin (DCX, santa cruz, goat origin 1:500) as a first antibody was reacted for one night after dehydrating separated hippocampus with hydrogen peroxide. And then, biotinylated anti-goat (vector, horse origin) was used as a second antibody, and color was formulated by using Diaminobenzidine after ABC reaction (ABC kit, vector). The effect on cell differentiation and enhancing neurite growth was identified by counting DCX-positive cells in the area of dentate gyrus in hippocampus.

The results are shown in Table 8.

TABLE 8

Effect on cell differentiation and enhancing neurite growth

| | D. Rhizoma:D. nipponica compared to the total weight | Amount (mg/kg) | DCX-positive cell (% of control) | Length of neurite (% of control) |
|---|---|---|---|---|
| Example 1 | 3.5:1 | 10 | 156.24 ± 9.40 | 125.38 ± 2.82 |
| | | 100 | 183.04 ± 12.67 | 142.59 ± 1.66 |
| Comparative Example 1 | D. Rhizoma crude extract | 10 | 126.84 ± 7.05 | 115.42 ± 3.60 |
| | | 100 | 132.81 ± 9.69 | 121.34 ± 2.56 |
| Comparative Example 2 | D. nipponica crude extract | 10 | 118.60 ± 8.37 | 120.48 ± 3.74 |
| | | 100 | 121.59 ± 8.13 | 120.57 ± 2.36 |
| Comparative Example 3 | 1:1 | 10 | 127.19 ± 7.23 | 120.48 ± 3.74 |
| | | 100 | 132.16 ± 9.61 | 129.63 ± 2.16 |
| Comparative Example 4 | 2:1 | 10 | 130.80 ± 8.67 | 124.08 ± 2.48 |
| | | 100 | 141.64 ± 7.85 | 131.75 ± 1.81 |
| Comparative Example 5 | 5:1 | 10 | 132.54 ± 10.34 | 121.64 ± 1.34 |
| | | 100 | 144.10 ± 9.32 | 130.12 ± 2.73 |
| Comparative Example 6 | 10:1 | 10 | 127.06 ± 11.46 | 123.39 ± 1.89 |
| | | 100 | 138.42 ± 9.29 | 129.61 ± 2.48 |
| Comparative Example 7 | 1:2 | 10 | 125.47 ± 14.38 | 119.42 ± 1.99 |
| | | 100 | 131.37 ± 11.94 | 126.74 ± 2.65 |
| Comparative Example 8 | 1:3.5 | 10 | 126.88 ± 10.43 | 120.74 ± 1.84 |
| | | 100 | 133.05 ± 9.59 | 122.38 ± 1.69 |
| Comparative Example 9 | 1:5 | 10 | 130.15 ± 9.29 | 125.42 ± 2.88 |
| | | 100 | 135.53 ± 10.74 | 131.41 ± 2.15 |
| Comparative Example 10 | 1:10 | 10 | 124.06 ± 9.86 | 121.72 ± 1.61 |
| | | 100 | 126.91 ± 10.34 | 124.63 ± 2.83 |

As shown in Table 8, in the area of dentate gyrus in hippocampus, *Dioscorea Rhizoma* (Example 1) showed increased the number of DCX-positive cells and the length of DCX-positive neurites than *Dioscorea nipponica* (Comparative example 2). Although the amount of *Dioscorea Rhizoma* was injected to Example 1 25% less than Comparative example 1, the number of DCX-positive cells and the length of DCX-positive neurites were increased approximately 25 to 40% and 1.6 to 17.3% more, respectively.

Furthermore, the number of DCX-positive cells and the length of DCX-positive neurites were increased approximately 18 to 27% and 3.3 to 9.2% more, respectively in Example 1 than Comparative example 5 (Dioscorea Rhizoma was injected 7.7% more than Example 1). The number of DCX-positive cells and the length of DCX-positive neurites were increased approximately 22.8 to 32.6% and 3.3 to 10% more, respectively in Example 1 than Comparative example 6 (*Dioscorea Rhizoma* was injected 17.4% more than Example 1). The number of DCX-positive cells and the length of DCX-positive neurites were increased approximately 20 to 30% and 1 to 8% more, respectively in Example 1 than Comparative example 4 (*Dioscorea Rhizoma* was injected 14.2% less than Example 1). It showed the significantly increasing the number of DCX-positive cells and the length of DCX-positive neurites than other Comparative examples.

Therefore it is found that a pharmaceutical composition of the present invention disorders comprising a mixed extract of *Dioscorea Rhizoma* and *Dioscorea nipponica* in a weight ratio of 3.5:1 has the effects on neuronal cell differentiation and enhancing neurite growth in the area of dentate gyrus compared to other mixed ratio.

EXPERIMENTAL EXAMPLE 5

Effect of the Herb Extracts on Enhancing the Secretion of NGF In Vivo

Hippocampi were separated from mice of the control group and the treatment group which was injected the mixed extract (*D.Rhizoma:D.nipponica*=3.5:1 extract) after completing the test of Experimental example 2. Anti-Nerve growth factor (NGF, abcam, rabbit origin 1:500) as a first antibody was reacted for one night and then biotinylated anti-rat (vector, goat origin) was used as a second antibody. After that, fluorescene-color was formulated by using streptavidin after ABC reaction (ABC kit, vector). The effect on enhancing the secretion of NGF was identified by counting NGF-positive cells in the area of hilus in hippocampus. The results are shown in FIG. 1.

Figure 1:
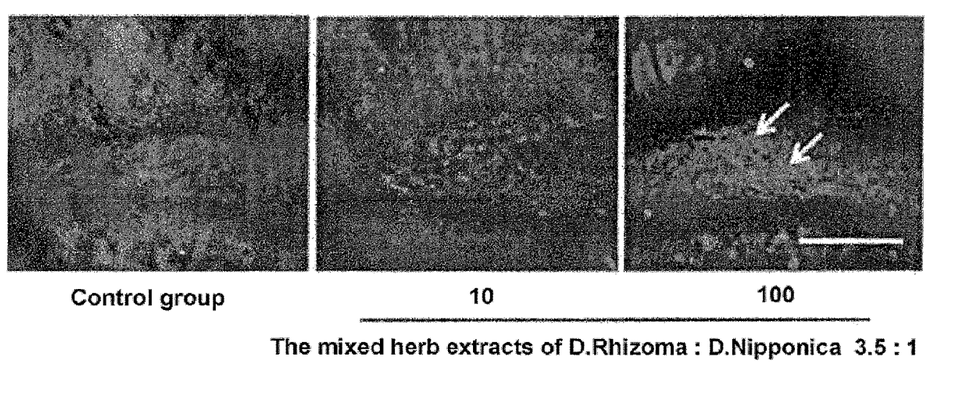
FIG. 1 is a photograph of a hippocampus region of the brain tissue illustrating the result from the evaluation of the secretion effect of nerve growth factor using NGF immunohistochemistry according to EXAMPLE 1.

As shown in FIG. 1, the herb extracts of Example 1 has the significant effect on enhancing the secretion of NGF in hippocampus.

Therefore it is found that a pharmaceutical composition of the present invention comprising a mixed extract of *Dioscorea Rhizoma* and *Dioscorea nipponica* in a weight ratio of 3.5:1 has the synergism compared to other mixed ratio. Thus, a phaimaceutical composition of the present invention may be used for preventing or treating neurodegenerative disorders including Alzheimer's disease, Creutzfeldt-Jakob disease, Huntington's disease, multiple sclerosis, Guillain-Barre syndrome, Parkinson's disease, Lou Gehrig's disease, paralytic dementia caused by gradual nerve cell death, diseases caused by progressive incontinentia, abnormalities in posture and exercise, progressive ataxia, muscular atrophy and weakness, and sensation and movement disorders.

Now, the composition comprising the herb extracts disclosed in EXAMPLE 1 will described in further detail by Formulation Examples. There have been no intentions to limit the claims but explain specifically.

FORMULATION EXAMPLE 1

Preparation of Injection

| | |
|---|---|
| Extract of Example 1 | 100 mg |
| Sodium metabisulfite | 3.0 mg |
| Methylparaben | 0.8 mg |
| Propylparaben | 0.1 mg |
| Sterile water for injection | q.s. |

To a mixture of the ingredients was added sterile water to form a total volume of 2 mL, and the solution was loaded to a 2 mL ampule and sterilized to give an injection.

FORMULATION EXAMPLE 2

Preparation of Tablet

| | |
|---|---|
| Extract of Example 1 | 200 mg |
| Lactose | 100 mg |
| Starch | 100 mg |
| Mg stearate | q.s. |

The ingredients were mixed and compressed into a tablet using a tableting method.

FORMULATION EXAMPLE 3

Preparation of Capsule

| Extract of Example 1 | 100 mg |
|---|---|
| Lactose | 50 mg |
| Starch | 50 mg |
| Talc | 2 mg |
| Mg Stearate | q.s. |

The ingredients were mixed and loaded to a gelatin capsule according to a typical method to afford a capsule.

FORMULATION EXAMPLE 4

Preparation of Liquid

| Extract of Example 1 | 1000 mg |
|---|---|
| Sugar | 20 g |
| Isomerase | 20 g |
| Lemon Flavor | q.s. |
| Purified water added to form a total volume of 100 mL | |

The above ingredients were mixed, loaded into a 100 mL brown vial and sterilized to afford a liquid formulation.

The invention claimed is:

1. A method for treating a neurodegenerative disorder in a subject in need thereof, comprising administering to the subject an effective amount of a pharmaceutical composition comprising (i) an extract of a mixture of Discorea Rhizoma and rhizome of *Dioscorea nipponica*, wherein the ratio of the Discorea Rhizoma to the rhizome of *Dioscorea nipponica* is 3.5:1, respectively, in the mixture; and (ii) a pharmaceutically acceptable carrier.

2. The method of claim 1, wherein the neurodegenerative disorder is selected from the group consisting of Alzheimer's disease, Creutzfeldt-Jakob disease, Huntington's disease, multiple sclerosis, Guillain-Barre syndrome, Parkinson's disease, Lou Gehrig's disease, paralytic dementia caused by gradual nerve cell death, and diseases caused by progressive incontinentia.

3. The method of claim 1, wherein the *Dioscorea* Rhizoma is a rhizome of *Dioscorea batatas* Decaisne or *Dioscorea japonica* Thunberg.

4. The method of claim 1, wherein the rhizome of *Dioscorea nipponica* is a rhizome of *Dioscorea nipponica* Makino.

5. The method of claim 1, wherein the pharmaceutical composition further comprises a suitable carrier, excipient or diluent selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

6. The method of claim 1, wherein the pharmaceutical composition is in a solid form.

7. The method of claim 1, wherein the pharmaceutical composition is in a liquid form.

8. The method of claim 3, wherein the *Dioscorea* Rhizoma is steamed and dried.

9. The method of claim 1, wherein the pharmaceutical composition comprises:
   (a) 100 mg of the extract;
   (b) 3.0 mg of sodium metabisulfite;
   (c) 0.8 mg of methylparaben; and
   (d) 0.1 mg of propylparaben;
   wherein the pharmaceutical composition is in an injectable form.

10. The method of claim 1, wherein the pharmaceutical composition comprises:
    (a) 100 mg of the extract;
    (b) 100 mg of lactose;
    (c) 100 mg of starch; and
    (d) a pharmaceutically acceptable amount of magnesium stearate;
    wherein the pharmaceutical composition is in a tablet form.

11. The method of claim 1, wherein the pharmaceutical composition comprises:
    (a) 100 mg of the extract;
    (b) 50 mg of lactose;
    (c) 50 mg of starch;
    (d) 2 mg of talc; and
    (e) a pharmaceutically acceptable amount of magnesium stearate;
    wherein the pharmaceutical composition is in a capsule form.

12. The method of claim 1, wherein the pharmaceutical composition comprises:
    (a) 100 mg of the extract;
    (b) 20 mg of sugar;
    (c) 20 mg of isomerase; and
    (d) a pharmaceutically acceptable amount of lemon flavor;
    wherein the pharmaceutical composition is in a liquid form.

13. The method of claim 1, wherein the pharmaceutical composition is administered at a dose from 0.01 g/kg to 10 g/kg.

14. The method of claim 1, wherein the pharmaceutical composition is administered orally, intrarectally, intravenously, intramuscularly, hypodermically, endometrially, or intracerebroventicularly.

* * * * *